United States Patent [19]
Amstutz et al.

[11] Patent Number: 5,156,627
[45] Date of Patent: Oct. 20, 1992

[54] COLLARLESS FEMORAL HIP PROSTHESIS

[75] Inventors: Harlan C. Amstutz, Pacific Palisades; J. Michael Kabo, Granada Hills, both of Calif.

[73] Assignee: Regents of the University of California, Oakland, Calif.

[21] Appl. No.: 32,737

[22] Filed: Mar. 30, 1987

[51] Int. Cl.$^5$ .............................. A61F 2/34
[52] U.S. Cl. ..................................... 623/23
[58] Field of Search ............... 623/11, 16, 18, 20, 623/22, 23

[56] References Cited

U.S. PATENT DOCUMENTS 4,459,708  7/1984  Buttazzoni .......................... 623/22

FOREIGN PATENT DOCUMENTS

| 0027159 | 4/1981 | European Pat. Off. | 623/23 |
| 0149527 | 7/1985 | European Pat. Off. | 623/23 |
| 2229812 | 1/1974 | Fed. Rep. of Germany | 623/27 |
| 2805305 | 8/1978 | Fed. Rep. of Germany | 623/22 |
| 2429010 | 2/1980 | France | 623/22 |

OTHER PUBLICATIONS

Tronzo "Total Hip Arthroplasty" J.B.J.S. vol. 53-A No. 7 Oct. 1971.
Spectron "The Spectron System Conversion Fem. Endoprosth.; The Technique" Richard 1978.

Primary Examiner—David Isabella
Attorney, Agent, or Firm—Poms, Smith Lande & Rose

[57] ABSTRACT

A femoral stem type hip joint prosthesis system includes a series of shoulderless or collarless, anatomically contoured stems of differnt sizes for firm implantation into the intramedullary canal of the femur; and a series of head units having variable neck lengths so that anatomically correct positioning of the head of the prosthesis may be obtained with varying depths of implantation of the stem, and normal anatomical variations. The stem may be smoothly tapered, and may have a rectangular cross-sectional configuration with substantially greater width in the medial/lateral direction than in the anterior/posterior direction. The stem may have a medical curvature of approximately six inches and a lateral curvature of approximately three inches adjacent its proximal or upper end, and this curved upper portion blends smoothly into a tapered lower section, having a centerline which is straight, and with the implanted portion of the stem being in the order of four and one-half inches or more in length.

24 Claims, 3 Drawing Sheets

COLLARLESS FEMORAL HIP PROSTHESIS

FIELD OF THE INVENTION

This invention relates to femoral hip prostheses.

BACKGROUND OF THE INVENTION

Problems with diseased and arthritic hip joints have been with the human race for many years. Since early in the present century, various proposals and operative techniques have been proposed for partial or complete replacement of the hip joint. An extensive article discussing the history of many hip joint prostheses is entitled "THARIES Surface-replacement Arthroplasty for the Arthritic Hip: Rebirth of an Earlier Concept?", by Dr. Harlan C. Amstutz et al., 1977.

When the problem with the hip joint is primarily at the mating surfaces of the joint, replacement of the surfaces is normally to be preferred, whereas, if the head of the femur has been weakened by necrosis or otherwise, the head may be removed, and a prosthesis having a head and a metal stem is implanted into the intramedullary canal at the upper end of the femur. However, the prostheses which have been proposed up to the present time have not been free of problems. Some of the stem-type prostheses have been subject to fatigue fracture, and the acrylic cement which has sometimes been employed to secure prostheses in place, occasionally fails.

With regard to stem-type prostheses, these are normally employed when the femoral head is severely diseased, as noted above, or when a stem in situ has failed and must be replaced. As shown in the article cited above, and in U.S. Pat. Nos. 4,101,985 and 4,141,088, stem-type prostheses normally have collars or shoulders to accurately position the head of the prosthesis relative to the surface of the femur where the head thereof has been removed. However, the presence of the collar or shoulder normally prevents the stem of the prosthesis from seating at full depth firmly into the engagement with the walls of the medullary canal, while fixing the longitudinal position of the prosthesis. However, because the stem does not necessarily engage the walls of the canal, it may shift laterally in its position whether or not it is initially cemented into place. In some cases, the geometry of the stem prosthesis is such that stress concentration points are established, leading to possible fracture of the stem prosthesis.

One medical technique which may usefully be employed in many cases involves removal and reattachment of the trochanter during the operation, with the trochanter being a major protruberance near the upper end of the femur, to which a number of muscles and ligaments are secured. This type of trochanteric osteotomy permits flexibility in the operation, as described in the article by Dr. Amstutz cited above. Now, some proposed femoral prostheses have very large cross-sectional stems toward the upper end of the femur adjacent the trochanter, necessitating the removal of bone in this area. Removal of bone adjacent the trochanter weakens the femur in this area, and makes the trochanter osteotomy procedure less practical; accordingly, femoral prostheses having enlarged upper portions are considered undesirable, from this standpoint as well as for other reasons.

Accordingly, a principal object of the present invention is to provide a stem-type femoral prosthesis which avoids the problems discussed hereinabove.

SUMMARY OF THE INVENTION

In accordance with one broad aspect of the invention, a stem-type femoral prosthesis is formed in two parts, with one part being a collarless, anatomically contoured stem formed in a series of successive sizes and with an external taper or other means for coupling to the head of the prosthesis; and with the second part being a series of heads having different distances from the center of the head to the mating internal taper or other means for coupling to the stem, so that the head may be located at a normal anatomical position relative to the leg, despite variations in the depth of penetration of the stem into the intramedullary canal of the femur, and normal variations in the anatomy of the patient.

In the determination of the correct anatomical contouring of the metal stem to match the intermedullary canal at the upper portion of the femur, a substantial number of X-rays were observed. Incidentally, because X-rays originate at a point source, X-ray negatives are normally an enlarged representation of the anatomy by a factor of 15% or 20%, for example, depending on the relative positions of the source, object, and film; and this must be taken into account in the selection of the proper prosthesis size by using enlarged templates corresponding to the various stem sizes and overlaying these templates on the patient X-rays. It may also be noted that it is customary to use the terms "medial" and "lateral" to refer to surfaces or parts of objects which are located toward the middle, and toward the side, respectively of the body. Similarly, the terms "anterior" and "posterior" are employed in reference to the front and back, respectively; and the terms "proximal" and "distal" refer to "close" and "remote", respectively, from the point of origin or attachment to a joint.

Returning to the anatomical configuration of the stem, a series of stems of approximately eight different sizes were developed, with the difference in length between sizes being about four millimeters, and thus, the length of the stem portion intended to be within the intramedullary canal of the femur ranging from a length of about 4.73 inches (about 12.0 centimeters) up to about 5.83 inches (14.8 cm). The stems all have a medial (inner) radius of curvature near the upper (proximal) end thereof of about six inches, and a lateral (outer) radius of curvature of about three inches. The center line of the stem is straight at its lower (distal) end, and the stem is tapered, with an approximate 5 degree taper in the medial-lateral plane and an approximate 2.6 degree taper in the anterior/posterior plane. The stem cross-section is preferably approximately rectangular, with rounded corners. At the larger, top end of the stem, the stem has a width (in the medial lateral plane) which is substantially greater than its thickness, with the width being about 1 inch for one of the intermediate sizes. Toward the smaller, distal end of the stem the cross-section becomes about square.

Concerning the coupling between the stem and the head of the prosthesis, the preferred method is a taper, such as a Morse taper, of about two or three degrees, with an external taper on the stem, and an internal taper on the head unit.

As noted above, a series of heads are provided, with different spacings of each of the heads from its associated internal taper. Thus, in a close spaced head, the internal taper may extend nearly through the head, while for the greatest spacing, the head may be mounted on a neck in which the internal taper is located. Thus, after firmly mounting the shoulderless or collarless stem in place, a proper anatomical positioning of the ball or head of the prosthesis may be accomplished by selecting a head unit with the proper effective neck length.

With regard to materials, the use of titanium or a titanium alloy is to be preferred, as there appears to be an affinity between bone and titanium, or titanium alloys. In this regard, it has sometimes been proposed to provide a surface coating of porous titanium or titanium mesh on orthopedic prostheses. However, if a stem-type prosthesis were to be fully coated in this manner, there could be bone ingrowth or bonding at the distal end of the stem at the area of furthest penetration into the femur. Under these conditions, the stem might assume the body load, and the upper part of the femur above the area of ingrowth or bonding could be subject to resorption, or wasting away of the bone substance. Accordingly, any external porous titanium or titanium mesh should preferably be limited in coverage to avoid this possible adverse effect.

Incidentally, prior to the insertion of the stem prosthesis for the first time, the head of the femur is removed, and the medullary canal is broached to receive the stem portion of the prosthesis. In this regard, a set of broaches is provided which correspond in configuration to the different size stems which are available. The broaching may be accomplished in two or more steps, with the sequential broaching steps employing broaches of progressively increasing size.

Other objects, features, and advantages will become apparent from a consideration of the following detailed description and from the accompanying drawings.

DETAILED DESCRIPTION

As mentioned above, the present invention in one aspect involves the use of an anatomically configured stem prosthesis which is matched to the configuration of the intramedullary canal in the upper portion of the femur, particularly in the medial lateral plane. In accordance with one aspect of the invention, it is desirable that the stem firmly engage the inner surfaces of the wall of the medullary canal. In order to accomplish this tight fit, a set of eight stems have been designed with these stems being anatomically configured to fit a wide range of human builds, from relatively small persons to very large persons.

In connection with the diagram of FIG. 1, and Tables I and II, as set forth below, the approximate dimensions of the various prostheses ranging from the smallest to the largest sizes are set forth. In addition, in the course of measuring X-rays of actual patients having different physical configurations, and developing the stem dimensions as set forth below, it was also determined that certain angles and certain dimensions for all eight of the prostheses were unchanged, despite the significant increase in the size and strength of the prostheses intended for larger persons.

With the foregoing background, reference will now be made to FIG. 1, in which the stem 12 forms one component, and the ceramic head 14 forms another component which mates with the stem 12 through a coupling which may be in the form of a Morse taper as discussed in greater detail hereinbelow. The stem of the prosthesis is tapered, as indicated by the cross-sectional views of FIGS. 2, 3 and 4, with the tapering in the medial-lateral plane being in the order of 5 degrees, and the tapering of the stem in anterior-posterior plane being in the order of 2.6 degrees. In addition, as indicated at reference numeral 16, the end of the stem 12 may be sharply chamfered to permit easier entry into the medullary canal.

One significant feature of the prosthesis of the present invention is that it has no collar or shoulder to prevent the firm seating and engagement of the stem prosthesis with the internal walls of the medullary canal, by the narrower side surfaces of the stem prosthesis. However, because of this slight uncertainty in the depth of penetration of the prosthesis, a series of heads 14 are provided for compensating for possible different depths of penetration of the stem, so that the proper anatomical position of the head may be achieved. Thus, as discussed in greater detail in connection with FIGS. 9 and 10 of the drawings, the effective neck length, as shown by the letters "NL" in FIG. 1 and as tabulated in Table II, may be varied from a short configuration, to a medium configuration, to a long configuration, with the long configuration of the head and effective neck length being employed when the penetration of the stem prosthesis is slightly greater than normal.

Certain dimensions which are employed throughout the entire set of stem prostheses include the 47.5 degree angle between the axis of the head and neck, as indicated by the dash-dot line 18, and the stem 12, and the 17.5 degree angle between a perpendicular 20 to the axis of the neck 22 and the plane 24 defining the start of the stem portion of the prosthesis which is intended to enter the intramedullary canal. Somewhat surprisingly, the optimum anatomical radius of three inches for the lateral surface 26 of the stem prosthesis is substantially constant for all sizes of the stem prosthesis, as is the radius of six inches for the medial surface 28 of the stem prosthesis. Certain non-critical radii, such as the radii on the medial and lateral surfaces of the neck 22, are also the same for all sizes of the stem prosthesis.

Table I, as set forth hereinbelow, includes the approximate dimensions for each size of the prosthesis, with references in Table I referring to the letters shown in FIG. 1, and in the cross-sectional views of FIGS. 3 through 4. It may be noted in passing that the cross-section of FIG. 2 is nearly square, near the distal end of stem.

TABLE NO. I

STEM MODULAR DIMENSIONS (Inches)

| Size | A | B1 | B2 | D1 | D2 |
|---|---|---|---|---|---|
| 1 | 4.73 | .313 | .238 | .425 | .450 |
| 2 | 4.89 | .360 | .263 | .472 | .500 |
| 3 | 5.05 | .407 | .288 | .519 | .550 |
| 4 | 5.21 | .454 | .313 | .566 | .600 |
| 5 | 5.36 | .501 | .338 | .613 | .650 |
| 6 | 5.52 | .548 | .363 | .660 | .700 |
| 7 | 5.68 | .595 | .388 | .707 | .750 |
| 8 | 5.83 | .642 | .413 | .754 | .800 |

NOTE:
Dimensions A, B1, B2, D1 and D2 are as shown in FIGS. 1, 3, and 4 of the Drawings.
NOTE: Re Tapers:
5 degree distal stem taper (Medial/Lateral Plane)
2.6 degree stem taper (Anterior/Posterior Plane)

TABLE II

NECK LENGTH MODULAR DIMENSIONS (Inches)

| Size | Short NL1 | Medium NL2 | Long NL3 |
|---|---|---|---|
| 1 | .926 | 1.084 | 1.241 |
| 2 | 1.006 | 1.164 | 1.321 |
| 3 | 1.086 | 1.244 | 1.401 |
| 4 | 1.166 | 1.324 | 1.481 |
| 5 | 1.246 | 1.404 | 1.561 |
| 6 | 1.326 | 1.484 | 1.641 |
| 7 | 1.404 | 1.564 | 1.719 |
| 8 | 1.486 | 1.644 | 1.801 |

NOTE:
Neck Length Dimension "NL" is as shown in FIG. 1 of the drawings.

Figures 5, 6:
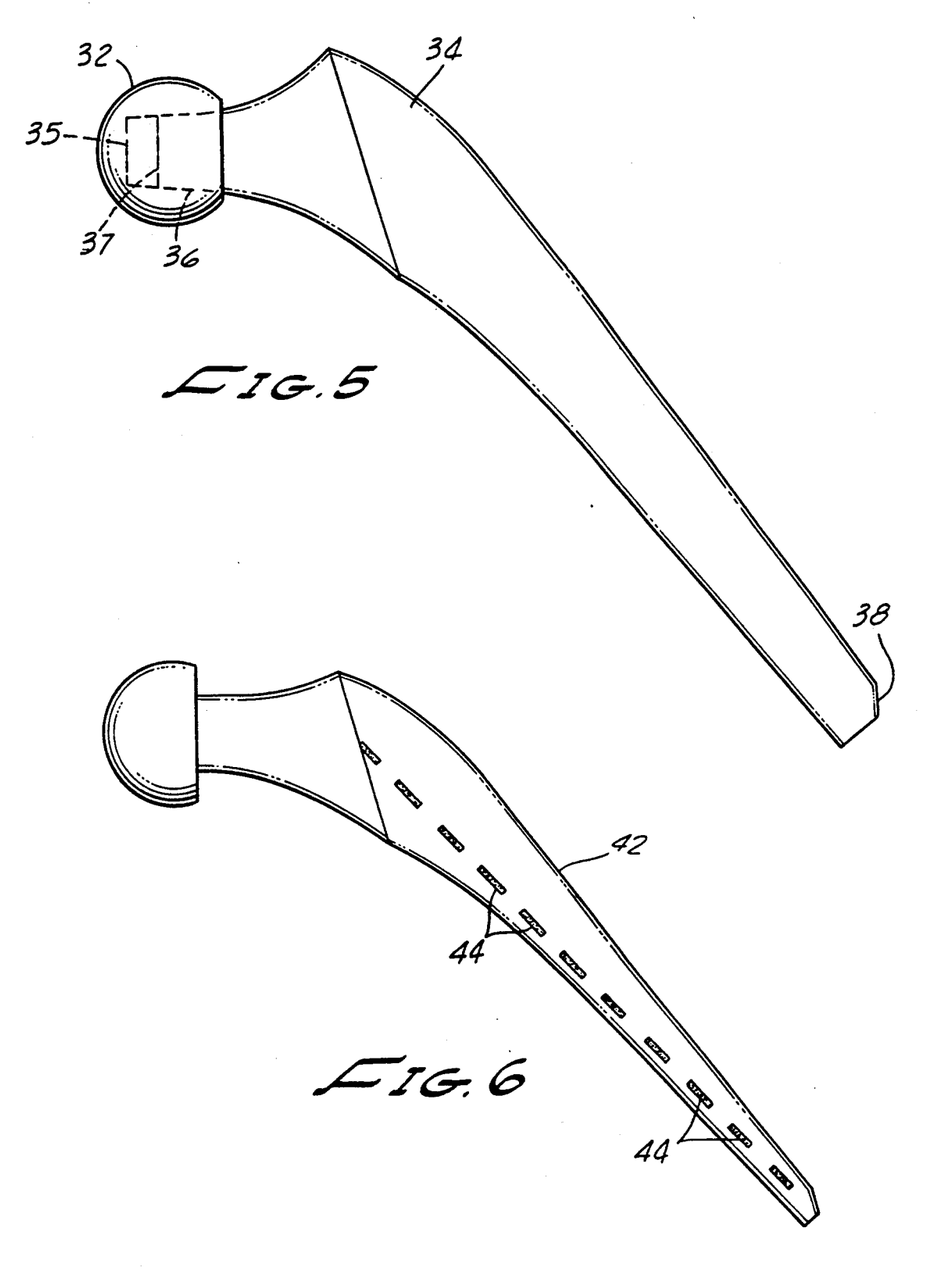
FIG. 5 is a side view of one of the larger stem prostheses in the series of different size prostheses employed in accordance with one aspect of the present invention.
FIG. 6 is a cross-sectional view of one of the smaller prostheses employed in accordance with the present invention.

FIGS. 5 and 6 are side views of the largest size, size 8 of the femoral prosthesis and the next-to-smallest size, size 2 thereof, respectively. With reference to FIG. 5, it may be noted that it is substantially longer than the prosthesis of FIG. 6, in addition to being substantially thicker throughout its length. Incidentally, the difference in length between successive sizes is approximately 4 millimeters, or 0.4 centimeters, which is equal to approximately 0.157 inch. This is somewhat more than 1/8th of an inch for each change in size, amounting to approximately one inch in difference in length between the size 8 stem prosthesis shown in FIG. 5, and the size 2 prosthesis shown in FIG. 6.

As mentioned above, the head 32 is removably secured to the stem 34 by a coupling 36 which may be in the form of a Morse taper, having a two or three degree angle, so that the parts 32 and 34 remain mated, following assembly by engaging the ball onto the tapered end of the stem.

Figures 1, 2, 3, 4:
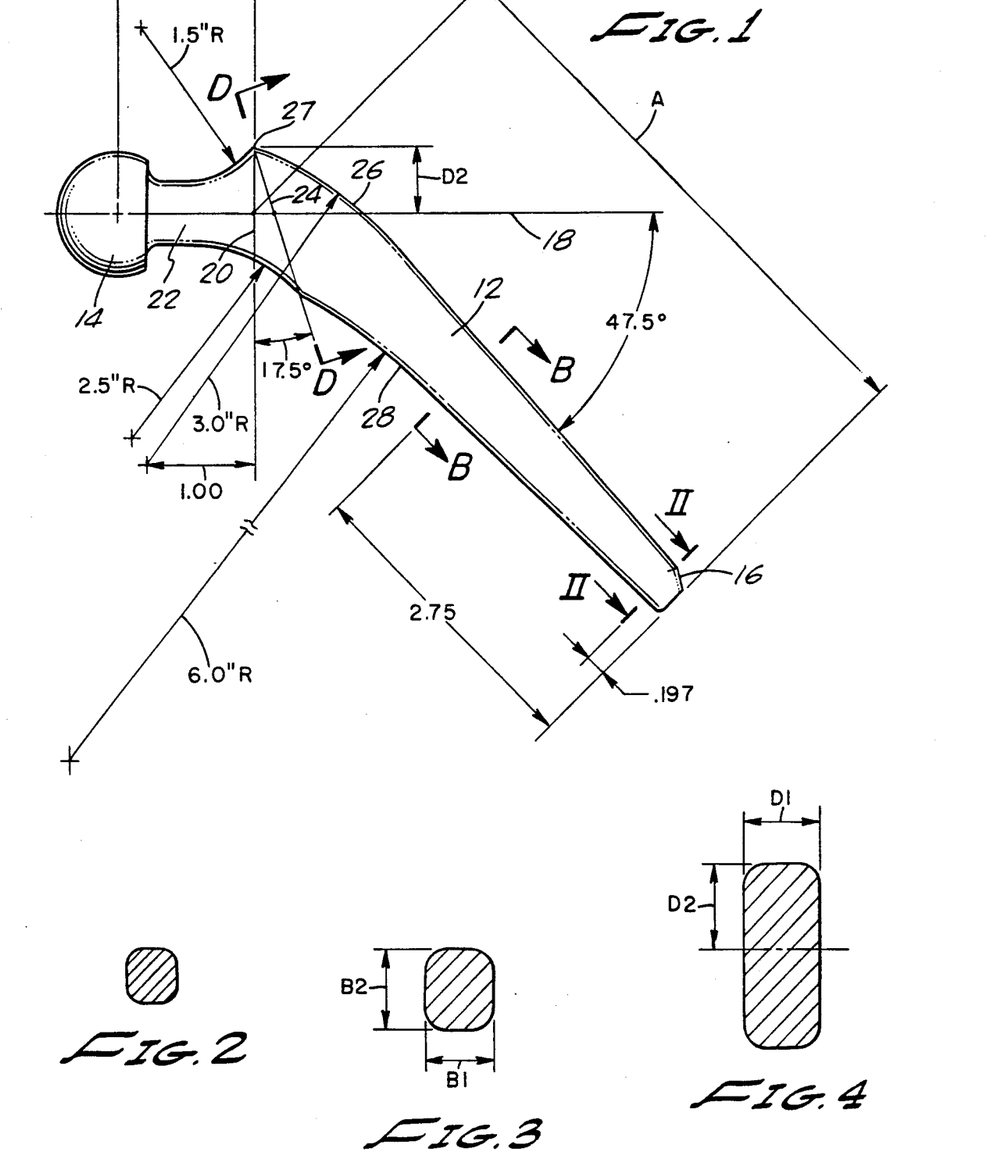
FIG. 1 is a diagram showing a side view, anterior-posterior, of a prosthesis illustrating the principles of the present invention, and giving key dimension designations for the different size femoral stem protheses which may be employed.
FIG. 2 is a cross-sectional view taken along lines II—II of FIG. 1.
FIG. 3 is a cross-sectional view taken along lines B—B of FIG. 1.
FIG. 4 is a cross-sectional view taken along lines D—D of FIG. 1.
Figure 9:
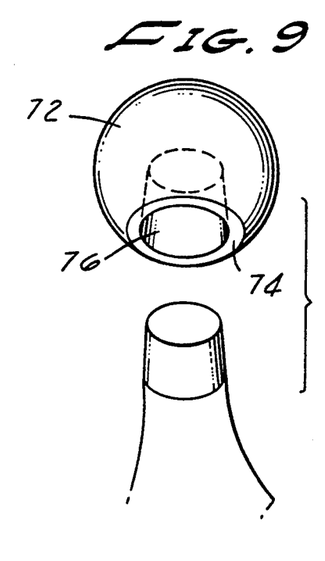
FIG. 9 illustrates one of three alternative heads for the prosthesis, with the head of FIG. 9 providing a medium effective neck length.

As indicated in FIG. 5 in dashed lines, the heads may have variable depth recesses, as indicated at the two reference numerals, 35 and 37, or as shown below in FIG. 9, the heads may be provided with a neck, to vary the effective "Neck Length" or "NL" as shown in FIG. 1 and tabulated in Table II.

It may also be noted that the distal end of the stem 34 is provided with a sharply tapered corner 38 to facilitate penetration or entry into the intramedullary canal at the upper end of the femur. Incidentally, in a preferred procedure, following the removal of the diseased head of the femur, the intramedullary canal is preferably broached preparatory to the implantation of the prosthesis into the canal.

Now, turning to FIG. 6, it has a reduced cross-section, and shorter length as compared with the larger, size 8 unit as shown in FIG. 5. In FIG. 6, the stem 42 may optionally be provided with a series of areas 44 which contain sintered particulate titanium material or fine titanium mesh formed into the surface of the stem 42 so as to be slightly raised relative to the surface thereof. These small areas 44 of titanium mesh or sintered particulate titanium, are intended to assist in bone ingrowth and the bonding of the entire length of the stem 42 to the femur.

As mentioned above, when full bonding or bone ingrowth occurs near the end of a stem prosthesis or under similar conditions, there is some possibility that the prosthesis will carry the full weight of the body directly to the lower end of the prosthesis where bonding with the bone had occurred, and that the upper portion of the bone enclosing the remainder of the prosthesis might be subject to resorption, with the bone substance wasting away. By providing only selected areas 44 for bone ingrowth or firm engagement, and by providing an anatomically contoured stem prosthesis, it is contemplated that the upper portion of the femur will remain at full strength and actively support the body weight.

Figures 7, 8:
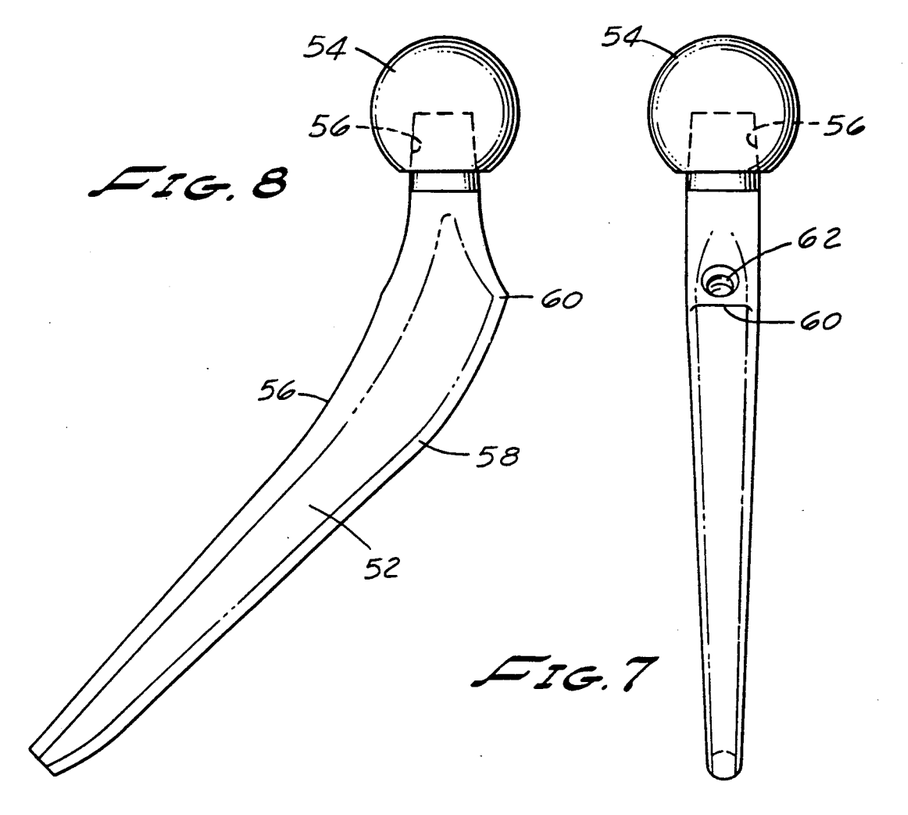
FIG. 7 is a side view of a femoral stem prosthesis and head assembly illustrating the principles of the present invention.
FIG. 8 is a view of the prosthesis of FIG. 7 taken 90 degrees displaced from the view of FIG. 7.

FIG. 7 shows a side view of a femoral prosthesis assembly in accordance with the present invention including the stem portion 52 and a head portion 54. Immediately below the head 54 is visible the start of the Morse taper 56 by which the head 54 is coupled to the stem 52. The dashed lines within the head 54 indicate that the taper extends most of the way through the head 54.

Incidentally, the heads employed herein may be metallic, ceramic, or metallic with a ceramic coating, or may be of other constructions with a suitable low friction outer surface. Concerning ceramic material, one suitable material is alumina, or aluminum oxide, in a dense, highly polished configuration. For metallic heads, cobalt chrome, or titanium may be employed.

FIG. 8 is a view of the femoral prosthesis of FIG. 7, taken from the right-hand side of the showing of FIG. 7. Accordingly, the concave medial side 56 of the stem prosthesis 52 is to the left in FIG. 7, the convex lateral side 58 is to the right in FIG. 7, and is the side which is visible in FIG. 8. It may be noted that just above the corner 60 of the prosthesis, there is an opening 62. This opening 62 provides a recess into which a driving member may be inserted so that, with the use of a mallet, the stem prosthesis may be firmly lodged in the upper end of the femur. The opening 62 may also be threaded, to facilitate removal of the prosthesis in the unlikely event that such removal would be necessary.

Figure 10:
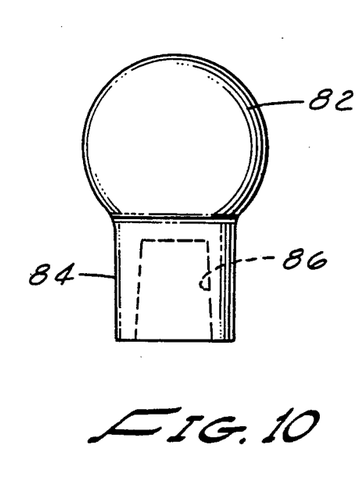
FIG. 10 shows an alternative head configuration with an additional skirt to provide a significantly greater neck length than the head configurations shown in FIGS. 9 and 5.

As mentioned above, the effective distance from the stem portion of the prosthesis to the center of the ceramic head may be varied, in order to provide an anatomically correct position for the head, despite slight variations in the depth of seating of the stem 52 into the intramedullary canal of the femur. FIGS. 9 and 10 show alternate head configurations to accomplish this purpose. More specifically, in FIG. 9, the head 72 is provided with a short, outwardly-extending collar 74 in which the taper 76 is located. Accordingly, using the head 72 of FIG. 9 instead of the head 32 with tapered recess 35 of FIG. 5, the head 72 of the prosthesis will effectively be shifted away from the stem portion of the prosthesis by a small increment. Similarly, the head 82, as shown in FIG. 10, has a longer neck 84 with the taper 86 being located within the neck 84, to further shift the center of the head 82 away from the stem portion of the prosthesis.

Referring back to FIG. 1, the designation "NL", refers to the "neck length", which extends from the corner of the stem prosthesis, designated by the reference numeral 27 in FIG. 1, to the center of the head 14 of FIG. 1, as measured along the centerline 18 of the head and neck of the assembly.

By way of explanation of Table II set forth hereinabove, the short neck length NL1 is achieved using a head having a relatively deep tapered recess, as indicated by the dashed line 35 as shown in FIG. 5. The medium neck length NL2 is indicated by the dashed line 37 in FIG. 5, and by FIG. 9 of the drawings; while the long neck length NL3 is illustrated in FIG. 10. It may be noted that the differences in neck lengths are the same for all of the eight prosthesis sizes, and the eight different size prostheses all have the same taper, so that each of the three different heads may be used with any of the stems to provide the neck lengths as indicted in Table II.

In practice, X-rays are initially taken of the femur of the patient, and a series of templates corresponding to the eight sizes of the stem prostheses are matched to the X-rays to obtain the best fit overlay. With the X-rays providing an image which is somewhat magnified, for example, about 15% or 20%, in view of the point source of the X-rays, correspondingly enlarged or magnified templates are employed to select the proper size stem for implantation.

In conclusion, it is to be understood that the foregoing detailed description relates to prostheses and a method for implanting them which illustrate the principles of the present invention. Various changes and departures from the specific embodiments as shown in the drawings and described hereinabove, may be made. The cross-section of the stem prostheses is preferbly nearly rectangular with rounded corners, but the rounding of the corners may be increased so that the shape is substantially oval, if desired. Thus, by way of example and not of limitation, the heads 54 may be formed of highly polished or highly smooth ceramic material, or of a metal ball, either provided with a thin coating of ceramic material or with a highly polished outer surface. Other low friction surface configurations may be used. As noted above, the recess 62 as shown in FIG. 8, may have smooth sidewalls, or may have threaded sidewalls to facilitate removal of the stem in the case such a procedure might prove necessary. The stem may be provided with small patches of sintered titanium, titanium mesh, or other similar porous material, slightly raised with respect to the remaining surface of the stem. While the entire stem is preferably formed of titanium or a titanium alloy for compatibility and affinity with human bone growth, the stem prostheses may be formed of other known high strength biologically-inert materials. In addition, instead of the taper, the heads may be secured to the stem portion of the prosthesis by fine threads, or by other close tolerance couplings of high mechanical strength, or the prostheses could be fabricated as integrated head and stem units. It is also noted that in some cases, the anatomical configuration of the patient is such that a slightly smaller size stem prosthesis should be used, although the femoral medullary canal is fairly large; and in such cases supplemental fixation may be provided through the use of cement. It is to be understood, therefore, that the present invention is not limited to the precise prosthesis arrangements and method as shown in the drawings and as described in the detailed description.

What is claimed is:

1. A set of hip prosthesis femoral assemblies comprising:

at least eight collarless stems of different sizes, each said stem having externally tapered means for coupling to a femoral head unit at a proximal end thereof, and having a stem configuration which is substantially rectangular in cross-section, and anatomically contoured in a medial-lateral plate, each said stem having a medial radius of curvature at said proximal end of approximately six inches, and a lateral radius of curvature at said proximal end of approximately three inches, and having a cross sectional dimension of said stem at said proximal end in said medial-lateral plane approximately equal to a corresponding dimension of an intramedullary canal at a corresponding proximal end of a femur, said stem being smoothly tapered to match an internal taper of said intramedullary canal such that depth of insertion of said stem in said intramedullary canal is determined solely by firm cementless engagement of said stem with walls of said intramedullary canal, toward a straight distal end of said stem; and a plurality of head units having internally tapered means for coupling to said externally tapered means on said stem, said head units having significantly different effective neck lengths from said stem to each said head unit;

whereby a substantially anatomically correct (1) best fit for said stem in said intramedullary canal and (2) position for said femoral head unit, may be provided, despite variations in a depth of implantation of said stem into said intramedullary canal.

2. A set of hip prosthesis femoral assemblies as defined in claim 1 wherein each said prosthesis is provided with a reduced diameter neck between said femoral head unit and said proximal end of said tapered stem.

3. A set of hip prosthesis femoral assemblies as defined in claim 1 wherein a set of more than six of said stems of progressively different sizes is provided.

4. A set of hip prosthesis femoral assemblies as defined in claim 1 wherein each said stem is tapered approximately five degrees in said medial/lateral plane and approximately 2 to 3 degrees in an anterior/posterior plane.

5. A set of hip prosthesis femoral assemblies as defined in claim 1 wherein each said stem is smoothly tapered throughout a length thereof and has a substantially greater cross-sectional dimension in said medial/lateral plane than in said anterior posterior plane, particularly in an upper portion of said stem.

6. A set of hip prosthesis femoral assemblies as defined in claim 1 wherein each said stem has a length from a point which is intended to be adjacent said proximal end of said intramedullary canal to said distal end of said stem which is greater than four and one-half inches.

7. A method of implanting hip prosthesis femoral components comprising the steps of:

taking an X-ray of a patient's upper femur and hip joint;

selecting one of a series of different sizes of anatomically contoured, shoulderless prostheses having a stem with a substantially rectangular cross-section and a smoothly tapered configuration, to obtain a best match to said patient's upper femur, said prosthesis having an external taper for mating with a corresponding femoral head of said prosthesis;

surgically exposing a hip joint and removing a femoral head of said hip joint to expose an intramedullary canal of said femur;

inserting said stem of said selected prosthesis and advancing said stem into said intramedullary canal to make firm cementless engagement with inner walls of said intramedullary canal, with a depth of said selected prosthesis being determined solely by engagement thereof with said canal inner walls;

selecting said corresponding femoral head from a series of femoral heads having internally tapered recess means for engaging said external taper, said series of femoral heads having different effective neck lengths, whereby said corresponding femoral head is a substantially anatomically correctly positioned head selected to compensate for variations in a depth of seating of said prosthesis;

assembling together said corresponding femoral head and said stem; and locating said corresponding femoral head of said prosthesis into said patient's hip joint.

8. A method of implanting hip prosthesis femoral components as defined in claim 7 wherein said stem selection step is accomplished using oversize templates conforming to said different size prostheses, and overlaying said templates on comparable scale oversize X-rays of said patient's hip joint and upper femur.

9. A method as defined in claim 7 further including the additional step of broaching said intramedullary canal prior to implantation of said prosthesis therein to enable a precisely contoured fit.

10. A method as defined in claim 7 wherein no cement is employed between said prosthesis and said inner walls of said intramedullary canal.

11. A method as defined in claim 7 wherein said stem selection step involves selecting a prosthesis having a stem with a cross-sectional dimension at a proximal end thereof in a medial lateral plane which is substantially equal to a corresponding dimension of said intramedullary canal at a corresponding proximal end of said femur, and said stem being smoothly tapered to match an internal taper of said intramedullary canal toward a straight lower end of said stem having a substantially straight centerline.

12. A method as defined in claim 7 wherein said stem selection step involves selecting a single prosthesis from a series of different prostheses of different sizes, with each said stem having a medial radius of curvature at a proximal end thereof of approximately six inches and a lateral radius of curvature of approximately three inches.

13. A method as defined in claim 7 further including the step of broaching said intramedullary canal prior to insertion of said stem.

14. A method as defined in claim 13 wherein said broaching step includes the steps of sequentially broaching aid intramedullary canal using broaches of increasing size matched with each said stem to be used.

15. A hip prosthesis femoral assembly comprising;

a collarless stem formed of a high strength biologically compatible metal, said stem having means for coupling to a femoral head unit at a proximal end thereof, and having a stem configuration which is substantially rectangular in cross-section, and anatomically contoured in a medial-lateral plane, said stem having a cross-sectional dimension at said proximal end in said medial-lateral plane approximately equal to a corresponding proximal end of a femur, said stem being smoothly tapered to match an internal taper of said intramedullary canal such that depth of insertion of said stem in said intramedullary canal is determined solely by firm cementless engagement of said stem with walls of said intramedullary canal, toward a straight distal end of said stem; and a plurality of head units having mating means for coupling to said coupling means on said stem, said head units having significantly different effective neck lengths from said stem to each said head unit;

whereby a substantially anatomically correct position for each said head unit may be provided, despite variations in a depth of implantation of said stem into said intramedullary canal.

16. A hip prosthesis femoral assembly as defined in claim 15 wherein said stem has a medial radius of curvature of approximately six inches, and a lateral radius of curvature of approximately three inches in a section of said stem adjacent an area of said engagement with said proximal end of said intramedullary canal.

17. A hip prosthesis femoral assembly as defined in claim 15 wherein a set of more than five of said stems of different sizes are provided, whereby a proper size may be selected to fit each individual partner.

18. A hip prosthesis femoral assembly as defined in claim 15 wherein said stem is smoothly tapered throughout a length thereof and has a substantially greater cross-sectional dimension in said medial/lateral plate than in an anterior posterior plane.

19. A hip prosthesis femoral assembly as defined in claim 15 wherein said coupling means constitute Morse tapers.

20. A hip prosthesis femoral assembly as defined in claim 15 wherein said stem has a length from a point intended to be adjacent said proximal end of said intramedullary canal to said distal end of said stem which is greater than five inches.

21. A hip prosthesis femoral assembly as defined in claim 15 further comprising a recess means on a lateral side of said stem adjacent said coupling means for facilitating firm implantation of said stem, and for possible removal thereof.

22. A method of implanting hip prosthesis femoral components comprising the steps of:

taking an X-ray of a patient's upper femur and hip joint;

selecting one of a series of different sizes of anatomically contoured, shoulderless prostheses having a stem with a smoothly tapered configuration, to obtain a best match to said patient's upper femur, said prosthesis having an external coupling for mating with a corresponding femoral head of said prosthesis;

surgically exposing a hip joint and removing a femoral head of said hip joint to expose an intramedullary canal of said femur;

precision broaching said intramedullary canal;

inserting said stem of said selected prosthesis and advancing said stem into said intramedullary canal to make firm cementless engagement with inner walls of said intramedullary canal, with a depth of said selected prosthesis being determined by engagement thereof with said canal inner walls;

selecting said corresponding femoral head from a series of femoral heads having mating coupling means for engaging said external coupling of said stem, and said series of femoral heads having effective neck lengths, to provide an anatomically correctly positioned head selected to compensate for variations in a depth of seating of said prosthesis and normal anatomical neck length variations;

assembling together said corresponding femoral head and said stem; and locating said corresponding femoral head of said prosthesis into said patient's hip joint.

23. A hip prosthesis femoral assembly comprising:

a collarless stem formed of a biologically compatible material, said stem having externally tapered means for coupling to a femoral head unit at a proximal end thereof, and having a stem configuration which is substantially rectangular in cross-section, and anatomically contoured in a medial-lateral plane, said stem having a medial radius of curvature at said proximal end of approximately six inches, and a lateral radius of curvature at said proximal end of approximately three inches, and having a cross-sectional dimension of said stem at said proximal end in said medial-lateral plane approximately equal to a corresponding dimension of an intramedullary canal at a corresponding proximal end of a femur, said stem being smoothly tapered to match an internal taper of said intramedullary canal such that depth of insertion of said stem in said intramedullary canal is determined solely by firm cementless engagement of said stem with walls of said intramedullary canal, toward a distal end of aid stem having a substantially straight centerline; and a plurality of head units having internally tapered means for coupling to said externally tapered means on said stem, said head units having significantly different effective neck lengths from said stem to each said head unit;

whereby a substantially anatomically correct position for said femoral head unit may be provided, despite variations in a depth of implantation of said stem into said intramedullary canal.

24. A prosthesis as defined in claim 23 wherein said stem is formed of titanium.

* * * * *

UNITED STATES PATENT AND TRADEMARK OFFICE
CERTIFICATE OF CORRECTION

PATENT NO. : 5,156,627
DATED : October 20, 1992
INVENTOR(S) : Harlan C. Amstutz; J. Michael Kabo It is certified that error appears in the above-identified patent and that said Letters Patent is hereby corrected as shown below:

Insert the following at line 17, column 1 of the specification:

--This invention was made with Government support awarded by the Veterans Administration. The Government has certain rights in this invention.--

Signed and Sealed this

Twenty-first Day of March, 2000

Attest:

Attesting Officer

Q. TODD DICKINSON

Commissioner of Patents and Trademarks